(12) United States Patent
Humele et al.

(10) Patent No.: US 8,294,126 B2
(45) Date of Patent: Oct. 23, 2012

(54) APPARATUS FOR STERILISING CONTAINERS

(75) Inventors: Heinz Humele, Thalmassing (DE); Jochen Krueger, Thalmassing (DE); Hans-Juergen Menz, Backnang (DE); Eberhard Foell, Nehren (DE)

(73) Assignee: Krones AG (DE)

( * ) Notice: Subject to any disclaimer, the term of this patent is extended or adjusted under 35 U.S.C. 154(b) by 498 days.

(21) Appl. No.: 12/106,117

(22) Filed: Apr. 18, 2008

(65) Prior Publication Data

US 2009/0045350 A1 Feb. 19, 2009

(30) Foreign Application Priority Data

Apr. 19, 2007 (EP) .................................. 07007977

(51) Int. Cl.
*G01N 23/00* (2006.01)
(52) U.S. Cl. ............... 250/492.3; 250/491.1; 250/492.1; 250/505.1; 250/396 R; 53/267; 53/426; 53/489; 422/22
(58) Field of Classification Search .................... 53/426, 53/267, 489; 422/22
See application file for complete search history.

(56) References Cited

U.S. PATENT DOCUMENTS

| | | | |
|---|---|---|---|
| 2,602,751 A | 7/1952 | Robinson | |
| 3,105,916 A * | 10/1963 | Marker et al. ................... 313/33 |
| 4,305,000 A | 12/1981 | Cheever ..................... 250/492.3 |
| 4,652,763 A * | 3/1987 | Nablo ........................ 250/492.3 |
| 4,680,447 A * | 7/1987 | Mahawili ..................... 392/408 |
| 4,983,849 A | 1/1991 | Thompson et al. | |
| 5,053,196 A * | 10/1991 | Ide et al. ......................... 422/28 |
| 5,163,487 A * | 11/1992 | Clusserath ....................... 141/92 |
| 5,414,267 A | 5/1995 | Wakalopulos ............. 250/492.3 |
| 5,928,607 A * | 7/1999 | Frisk ................................ 422/29 |
| 6,028,315 A * | 2/2000 | Bailey et al. ............. 250/455.11 |
| 6,030,578 A * | 2/2000 | McDonald ....................... 422/24 |
| 6,139,796 A * | 10/2000 | Kristiansson et al. .......... 422/22 |
| 6,209,591 B1 * | 4/2001 | Taggart ............................ 141/89 |
| 6,221,216 B1 * | 4/2001 | Nablo et al. ............. 204/157.15 |
| 6,407,492 B1 * | 6/2002 | Avnery et al. ................. 313/420 |
| 7,010,900 B2 * | 3/2006 | Grossmann et al. ............ 53/167 |
| 7,520,108 B2 * | 4/2009 | Kristiansson et al. .......... 53/426 |
| 7,767,987 B2 * | 8/2010 | Eguchi et al. ............. 250/492.3 |

(Continued)

FOREIGN PATENT DOCUMENTS

BE 1011263 A6 * 6/1999

(Continued)

OTHER PUBLICATIONS

Icke et al., "Cold, Dry Electron Beam Sterilization for Aseptic Filling of PET Bottles", Advanced Electron Beams, Aseptipak, Feb. 2007, Orlando.

(Continued)

*Primary Examiner* — Michael Logie
(74) *Attorney, Agent, or Firm* — Hayes Soloway P.C.

(57) ABSTRACT

An apparatus (1) for sterilizing containers (10), comprising a treatment head (5) which has an exit window (8) through which charge carriers can pass, comprising a charge carrier generation source which generates charge carriers, and comprising an acceleration device (6) which accelerates the charge carriers in the direction of the exit window (8). According to the invention, the cross section of the treatment head (5) is dimensioned such that the treatment head (5) can be guided through the mouth of the container (10), and the acceleration device (6) accelerates the charge carriers in such a way that the charge carriers exiting from the exit window (8) can be aimed preferably directly onto an inner wall (15) of the container (10).

34 Claims, 9 Drawing Sheets

U.S. PATENT DOCUMENTS

| | | | |
|---|---|---|---|
| 2001/0010145 A1* | 8/2001 | Tawa et al. | 53/425 |
| 2004/0234028 A1* | 11/2004 | Hansen et al. | 378/69 |
| 2005/0158218 A1* | 7/2005 | Dumargue et al. | 422/121 |
| 2006/0186350 A1* | 8/2006 | Fontcuberta et al. | 250/492.1 |
| 2006/0192140 A1* | 8/2006 | Nablo et al. | 250/492.1 |
| 2007/0237672 A1* | 10/2007 | Colato et al. | 422/28 |
| 2008/0073549 A1* | 3/2008 | Avnery | 250/397 |
| 2008/0138243 A1* | 6/2008 | Kristiansson et al. | 422/23 |
| 2008/0310596 A1* | 12/2008 | Lu et al. | 378/141 |
| 2009/0045350 A1* | 2/2009 | Humele et al. | 250/455.11 |

FOREIGN PATENT DOCUMENTS

| | | |
|---|---|---|
| DE | 198 82 252 | 5/2000 |
| DE | 101 34 037 | 7/2001 |
| DE | 102 36 683 | 2/2004 |
| DE | 10236683 A1 * | 2/2004 |
| EP | 0 054 016 | 6/1982 |
| EP | 0885142 | 12/1998 |
| EP | 1 120 121 | 8/2001 |
| FR | 2 815 769 | 4/2002 |
| GB | 2 271 347 | 4/1994 |
| JP | 51-163399 | 12/1976 |
| JP | 9-99922 | 4/1997 |
| JP | 11-248900 | 9/1999 |
| JP | 11281798 | 10/1999 |
| JP | 200500103 | 1/2000 |
| JP | 2002-255125 | 9/2002 |
| JP | 2003121595 A * | 4/2003 |
| JP | 2004-53509 | 2/2004 |
| WO | WO 97/07024 | 2/1997 |
| WO | WO 02/36437 | 5/2002 |
| WO | WO 2004/013889 | 2/2004 |
| WO | WO 2007/072575 | 6/2007 |

OTHER PUBLICATIONS

Japanese Official Action, dated Jan. 6, 2011.
European Search Report, dated Apr. 13, 2011.
Japanese Official Action + translation, dated May 17, 2011, mailed May 23, 2011, Japanese Patent Appln. No. 2008-109617 (7 pgs).
Chinese Office Action, dated Sep. 21, 2011 (14 pgs).
European Office Action, dated Jan. 26, 2012 (4 pgs).

* cited by examiner

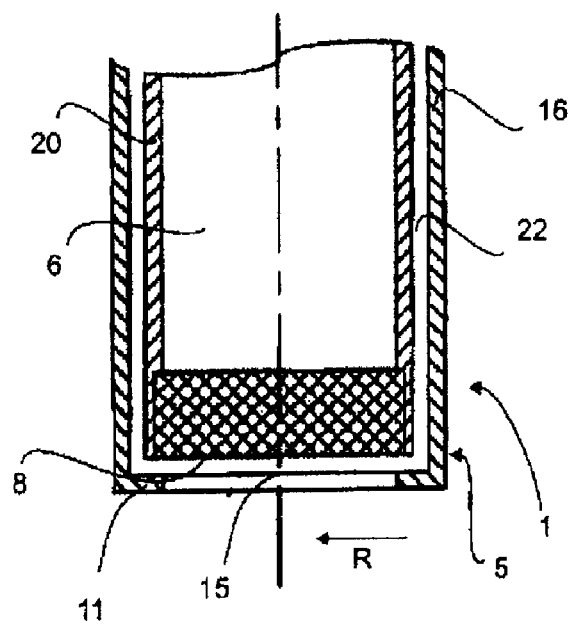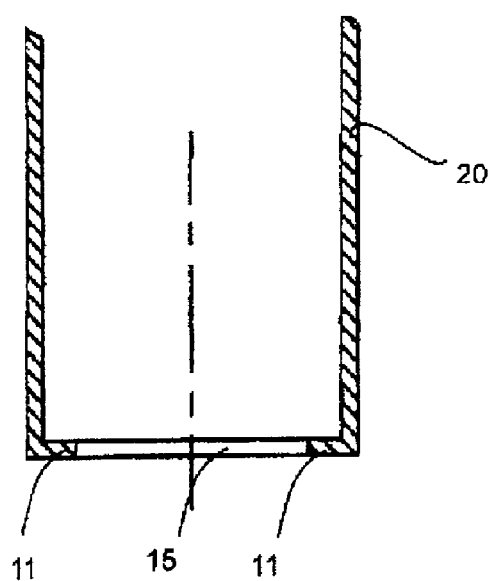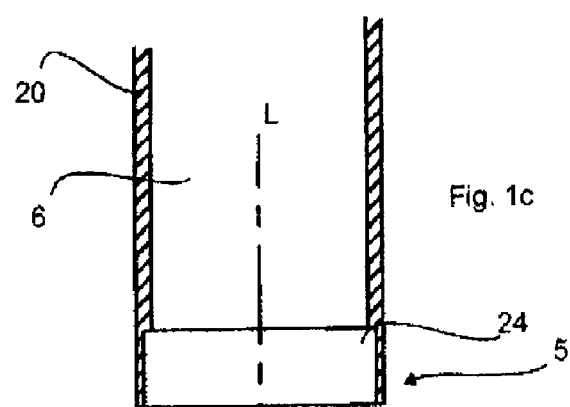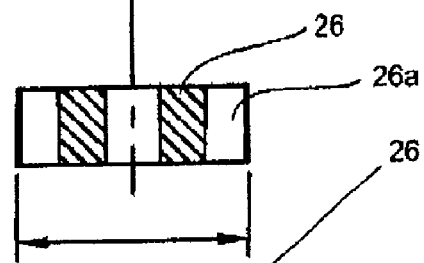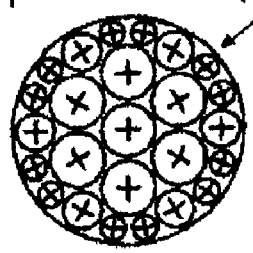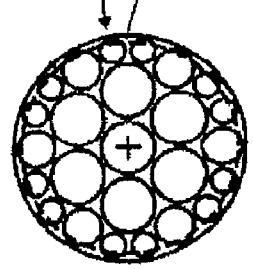

APPARATUS FOR STERILISING CONTAINERS

The present invention relates to an apparatus for sterilising containers, or more precisely for sterilising containers before they are filled. Specifically, the apparatus according to the invention is intended to sterilise the inner wall of containers to be filled, particularly bottles which have a mouth.

When foodstuffs are filled into a container, it is necessary to sterilise the container itself. For example, it is known to sterilise the inner wall of containers using steam or hydrogen peroxide. However, such methods are associated with disadvantages since treatment with hydrogen peroxide for example may lead to softening of the material. It has therefore been known from the prior art for a long time to sterilise the containers by means of charge carriers such as, in particular, electron beams.

JP 2002-255125 discloses an apparatus for sterilising containers. In said document, a radiation source is provided outside the container and directs radiation into the interior of the container. JP 2001-225814 also discloses a corresponding apparatus for sterilising the inner wall of containers, in which a radiation source emits radiation into the container from outside.

FR 2 815 769 discloses an electron beam source which emits two electron beams.

DE 198 82 252 T1 describes a technique for sterilising the interior of a container by means of electrons. Again, an electron beam source is provided which directs radiation into the interior of the container from outside.

These aforementioned apparatuses have the disadvantage that the radiation always enters the container from outside through the mouth thereof, and thus its beam direction can be varied only with difficulty within the interior of the container.

EP 0 885 142 B1 discloses a method for sterilising packagings for flowable goods. These are in particular packagings with one open side. In this method, high acceleration voltages are to be avoided, since X-rays are produced as an undesirable side effect of these high acceleration voltages and said X-rays in turn have to be shielded by a lead screen. In order to achieve a uniform internal cleaning effect, EP 0 885 142 B1 proposes to use a gas stream which is in contact with an electron beam and in this way helps the electrons to reach the inner wall of the container. However, the method described in EP 0 885 142 B1 is not suitable for cleaning the interior of bottles or in general containers with a mouth diameter, since the electron beam source described in EP 0 885 142 B1 would not be able to pass through this mouth and in any case could not enter this container together with the air tube described in EP 0 885 142 B1 which produces the air stream in the interior of the container.

The object of the present invention is therefore to provide an efficient apparatus and a method for cleaning the interior of containers with a mouth cross section which is narrower than the container cross section.

According to the invention, this is achieved by an apparatus according to claim 1, an arrangement according to claim 15 and a method according to claim 20. Advantageous embodiments and further developments form the subject matter of the dependent claims.

The apparatus according to the invention for sterilising containers comprises a treatment head which in turn has an exit window through which charge carriers can pass. Also provided is a charge carrier generation source which generates charge carriers, and an acceleration device which accelerates the charge carriers in the direction of the exit window.

According to the invention, the cross section of the treatment head is dimensioned such that the treatment head can be guided through the mouth of the container, and the acceleration device accelerates the charge carriers in such a way that the charge carriers exiting from the exit window can be aimed preferably directly onto an inner wall of the container.

The charge carriers are in particular electrons, but it would also be conceivable to use other charge carriers, such as ions.

In contrast to the cited prior art, use is therefore made of acceleration voltages which are high enough for the exiting electron beam to hit the inner wall of the container directly, without the interposition of a gas stream which is activated by the electron beam for a sterilising effect. An exit window is to be understood to mean a device which closes off in an airtight manner the interior of the apparatus, i.e. the area between the charge carrier generation source and the exit window, but through which the charge carriers, in particular the electrons, can still pass. It should be noted that the electrons exiting from the exit window are considerably slowed, so that significantly higher energies and acceleration voltages are used compared to the apparatus known from EP 0 885 142 B1.

In order to generate the electron beam, use is preferably made of a compact electron beam unit with an emitting finger which, as mentioned above, is dimensioned such that it can dip into the bottle in order thus to apply an electron cloud with the lowest possible energy onto the inner surface of the (PET) bottles. In the case of a rotating arrangement, it would be possible for operating units for the apparatus, such as e.g. transformers or power supply units for the electron beam generators, also to rotate on a carousel, as a result of which the supply of high voltage is simplified at the same time. In one preferred embodiment, the exit window and the acceleration device are arranged within an outer housing and this outer housing is dimensioned such that it can be guided through the mouth of the container. The treatment head is thus provided at the lower end of this outer housing, and it is also possible for the treatment head to be formed in one piece with the outer housing. Preferably, the entire outer housing including the treatment head thus has a cross section which is able to be introduced through the mouth of a container. The cross section of the treatment head may be of any shape. With particular preference, the apparatus has a circular cross section with a diameter of less than 40 mm, preferably less than 30 mm and particular preferably less than 25 mm.

Preferably, the entire apparatus is surrounded by a shielding device and in particular by a lead screen, in order to prevent any escape of X-ray radiation and thus to prevent harmful effects on users.

In a further preferred embodiment, the apparatus comprises an inner housing within which the acceleration device is arranged, and the outer housing surrounds this inner housing. With particular preference, a vacuum is applied in the interior of this inner housing, within which preferably the charge carrier generation source and the acceleration device are provided. Particularly preferably, a chamber which extends as far as the treatment head is formed between the outer housing and the inner housing, through which chamber a medium and in particular a gaseous medium can be guided. This gaseous medium serves in particular to cool the exit window, and for this purpose the gaseous medium is guided along the inner housing as far as the treatment head and also past the exit window. Preferably, therefore, a chamber in the form of one channel or a plurality of channels is formed between the outer housing and the inner housing, a lower end section of the outer housing particularly preferably being formed in such a way that the gas stream is also guided for example in the radial direction of the apparatus and thus also past the exit window. It is pointed out that the stream of gaseous medium does not or at least does not directly reach the inner wall of the container, but instead, as already mentioned, serves in particular for carrying past the exit window.

Advantageously, the gaseous medium is selected from a group of gaseous media comprising helium, nitrogen, argon, carbon dioxide, mixtures thereof or the like.

With particular preference, the exit window is made from a material selected from a group of materials comprising titanium, quartz glass, diamond, combinations thereof and the like.

In this embodiment, therefore, at least part of the apparatus is of double-walled design, wherein a gas or air is provided between the outer housing and the inner housing in order to cool the steel tube, i.e. the inner housing and the window. As already mentioned, the interior of the inner housing is evacuated and preferably has a titanium window at the end as the exit window. In a further preferred embodiment, the exit window has a thickness which is between 3 µm and 30 µm, preferably between 4 µm and 25 µm and particularly preferably between 5 µm and 20 µm. It is thus possible to use for the exit window a window film made for example from titanium having thicknesses of 8 µm, 10 µm, 13 µm or 15 µm. However, it is also possible to use another suitable material. This exit window or the window film is welded in a vacuum-tight manner to the inner housing, which is likewise made of a suitable material (such as e.g. also of titanium). It is possible in this case for the exit window to be placed over the opening of the inner housing in an unsupported manner, but it is also possible for a supporting structure to be used, such as a perforated plate for example, which carries the exit window. In the case of using a supporting structure for the exit window, it is also conceivable for the supporting structure to be cooled by a suitable liquid which is conveyed towards and away from the supporting structure through one or more channels between the inner housing and the outer housing.

In one preferred embodiment, the exit window has a uniform thickness over its entire surface. However, depending on the specific application, it would also be possible for the thickness to vary, for example to increase from the outside towards the inside. For example, it is also possible for the window film to have different thicknesses over its surface, for example varying between 4 and 13 µm or even in the form of a thickness perforation in lines or dots. In this way, it is possible to obtain electrons reaching the atmosphere, i.e. the outer side of the exit window, at different speeds, and hence a scattered field which differs from a conventional scattered field.

As mentioned above, different gases may be used as the cooling gas. In this way, an improved heat conduction of the gases can be achieved, in particular with helium. However, it would also be possible to influence the conditions for the electrons in the atmosphere, i.e. after exiting from the exit window. For example, the use of helium as the atmosphere leads to longer ranges of the electrons, since helium has a lower density than air. Furthermore, the treatment chamber, i.e. the interior of the container, can also be made inert through supplying the gases, which in turn leads to a reduction in ozone production.

As the beam generator, use may be made of either an open or closed electron beam unit, which is known for example from X-ray tubes or the like. The electron source itself may be formed of a point-type or area-type electron source, to which the inner housing or emitting finger is directly attached.

The apparatus according to the invention will hereinafter also be referred to as the emitting finger.

In a further advantageous embodiment, the apparatus comprises a deflection device for deflecting the charge carriers. With particular preference, this deflection device is arranged between the charge carrier generation source and the exit window. An electromagnetic deflection of the electrons can thus take place before the exit window, in order additionally to impose a preferred direction on the electrons in the direction of the bottle wall. In this way, it is possible to distribute the dose of radiation more uniformly over the inner surface of the container. It is also possible in this way to guide the electron beam uniformly over the entire exit surface of the exit window in order thus to achieve a more uniform load on the exit window as a whole and thus to prevent so-called hotspots on the window. However, it is also conceivable for the deflection unit to be arranged after the exit window in the direction of the electron beam.

Preferably, the inner housing has an increased inner diameter in the region of the treatment head, in order to facilitate this aforementioned deflection of the charge carriers.

Furthermore, with particular preference, the treatment head can move relative to the containers in a longitudinal direction of the container. In this way, a larger surface area of the inner wall of the container can be sterilised in one pass.

In a further advantageous embodiment, the treatment head can rotate relative to the container. This is particularly advantageous when the charge carriers also exit in a preferred radial direction relative to the treatment head. In a further advantageous embodiment, the treatment head can move relative to the container in a radial direction of the container. It is thus possible for example for the treatment head itself or the apparatus to be pivoted about a predefined pivot axis during the sterilisation process, or for the container itself to be pivoted relative to the treatment head. With particular preference, in this case, a pivot axis is provided in a region of the mouth of the container or slightly above the mouth of the container. In this way, the treatment head can be brought into the vicinity of the inner wall of the container.

The present invention also relates to an arrangement for treating containers by means of at least one apparatus of the type described above. Preferably, a plurality of the above-described apparatuses are arranged next to or behind one another in order to be able to sterilise a plurality of containers simultaneously. It is possible for example to form the entire arrangement as a rotating unit or linear unit, wherein a treatment chamber is provided which serves for sterilising the interior of beverage bottles by means of electron beams. It is thus also possible to integrate the apparatus according to the invention in a stretch-blowing machine or a filling device or to arrange it as a stand-alone unit in order to be able to retrofit existing lines or arrangements.

Preferably, the arrangement comprises a device for filling containers and the apparatus according to the invention is arranged upstream of this device.

Furthermore, the arrangement may comprise a displacement device which displaces the containers in the longitudinal direction of the containers relative to the apparatus. In principle, it would also be possible to maintain the height position of the containers and to displace only the apparatus in the longitudinal direction of the containers. However, since the apparatus or the emitting finger is of relatively complex design and is also usually supplied with high voltages, it is preferable to keep said apparatus stationary and instead to displace the containers relative to the apparatus.

Moreover, the apparatus is advantageously arranged between an expansion device for the containers and a device for filling the containers. A sterilisation of this arrangement is thus carried out after the expansion of the containers or the blowing of the containers.

Advantageously, the arrangement comprises a plurality of apparatuses of the type described above, wherein these individual apparatuses are particularly preferably arranged along a circular path. However, it would also be possible to arrange a plurality of apparatuses along a substantially straight path, for example parallel to a conveyor belt running in a straight direction.

In a further advantageous embodiment, the arrangement comprises a further sterilising apparatus for sterilising an outer wall of the containers. In this way, it is possible to carry out not only an internal sterilisation but rather also an external sterilisation of the containers.

In this case, with particular preference, the further sterilising apparatus is arranged upstream of the aforementioned apparatuses in the transport direction of the containers. This means that preferably firstly an external sterilisation of the containers is carried out, and then an internal sterilisation. Preferably, the further sterilising apparatus is an apparatus which irradiates the containers with charge carriers. However, other principles of sterilisation would also be possible in addition.

Preferably, the further sterilising apparatus is arranged in a stationary manner. This means that the containers are moved past this stationary sterilising apparatus. Preferably, in particular the peripheral wall and optionally also the neck region of the containers are sterilised by the further sterilising apparatus.

In a further advantageous embodiment, the further sterilising apparatus is arranged in a sterile chamber.

In a further preferred embodiment, the arrangement comprises a transport carousel which conveys the containers past the further sterilising apparatus. The containers are thus guided along a circular path. More specifically, preferably a plurality of transport carousels are provided which transfer the containers to one another. Preferably, this transport carousel comprises rotary devices which rotate the containers about their longitudinal axis. By providing these rotary devices, it is possible to sterilise a larger peripheral area of the containers.

The present invention also relates to a method for sterilising containers, wherein charge carriers are generated in an apparatus for sterilising the containers and are accelerated in the direction of an exit window, wherein this exit window is arranged in a treatment head. According to the invention, the treatment head of the apparatus is introduced through a mouth of the container into the interior of the container and accelerated charge carriers from the treatment head are aimed directly onto the inner wall of the container and the container is preferably moved relative to the treatment head.

Preferably, the charge carriers are deflected in a radial direction of the container or of the apparatus before reaching the exit window. For this deflection, use may be made of coils or the like.

Further advantages and embodiments can be seen in the appended drawings:

In the drawings:

FIG. 1a shows a partial view of an apparatus according to the invention for sterilising containers;

FIG. 1b shows an outer housing for the apparatus of FIG. 1a;

FIG. 1c shows an inner housing for the apparatus of FIG. 1a;

FIG. 1d shows a supporting body with an exit window for the apparatus of FIG. 1a;

FIG. 1e shows a plan view of the supporting window of FIG. 1d;

FIG. 1f shows a plan view of the exit window of FIG. 1a;

Figure 1G:
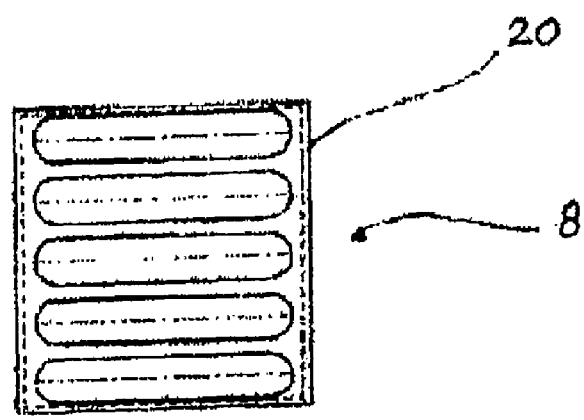
FIG. 1g shows a further embodiment of a supporting window.

FIG. 1a shows part of an apparatus according to the invention for sterilising containers. This apparatus comprises at its lower end a treatment head 5, on which there is provided an exit window 8 through which an electron beam can exit. Here, as is customary in the prior art, firstly the electrons are generated for example by means of a tungsten cathode. These electrons are then accelerated via an acceleration device 6 (not shown in detail). As the electron generation source, use may be made of point-type or area-type electron sources.

The apparatus 1 for sterilising containers comprises an outer housing 16 and an inner housing 20 and is thus of double-walled design. A gap 22 is formed between the outer housing 16 and the inner housing 20, along which gap it is possible for air, another gaseous medium or even a liquid medium to be guided. This air gap 22 may be designed to run in the circumferential direction, but it is also possible for a plurality of channels 22 to be provided. In principle, it is possible for the jet of gas to be guided past the exit window 8 in the radial direction R during operation of the apparatus 1, but it is also possible for the gas stream to be guided past the exit window 8 in the period in which the apparatus 1 is not active and/or the radiation source is not active. In this way, it is possible to prevent the exiting electron beam from being influenced by the air stream. It is pointed out that the gas stream serves exclusively for cooling the exit window and not for guiding the electron beam.

In principle, the radiation stream in the case of an optimally selected acceleration voltage is the critical factor for generating the respectively required dose in the container in the shortest possible time. In the exit window 8, however, this radiation stream leads to losses which, depending on the design of this exit window 8, sooner or later also limit the maximum radiation power of the electron beam unit or of the apparatus 1. However, with the described air, gas or liquid cooling, the necessary cooling of the exit window can also be ensured. In other words, in order to achieve the maximum possible radiation stream, i.e. the maximum possible throughput, the number of radiation units should be minimised and/or the cycle time should be increased. It would also be possible to improve the scattering geometry in the atmosphere, i.e. outside the exit window 8.

The electrons are accelerated to energy in a range from 100 keV-200 keV, preferably between 120 keV and 180 keV and preferably 130 keV and 170 keV.

FIG. 1*b* shows an outer housing 20 for an apparatus 1 according to the invention. It can be seen that walls 11 which protrude radially inwards are provided at the lower end of the outer housing 20. These walls 11 serve to guide air or gas, i.e. they result in at least some of the gas also being guided past the exit window 8. These walls 11 also form an opening 15, through which the generated electron beam can pass outwards.

However, it would also be possible to supply gas on one side of the inner housing 20 and to convey said gas away again on the other side of the inner housing 20.

FIG. 1*c* shows an inner housing 20. This inner housing 20 has at its lower end or on the treatment head 5 a recess 24 for receiving the exit window 8 or a supporting body 26 of the exit window 8.

FIG. 1*d* shows a supporting body 26 which serves for supporting the actual exit window 8 shown in FIG. 1*f*. In this embodiment, this supporting body 26 forms a plurality of channels 26*a*, through which the electron beam can pass. In addition, the supporting body 26 may have channels through which a cooling fluid or a cooling gas can be guided.

The actual exit window 8 shown in FIG. 1*f* is for example welded to the supporting body 26.

Different embodiments are conceivable for the inner housing 20 and the apparatus 1 as a whole. For instance, it is possible to produce the apparatus for example from quartz glass, i.e. in particular to produce the inner tube 20 from quartz glass. In this case, for example, a thin quartz glass film can be fused in as the exit window 8. Such films having a thickness of 20 µm are already known from the prior art. The density of such windows is in the region of 2.2 g/cm$^3$, corresponding to 44 g/cm$^2$. This corresponds to the surface density of a titanium film having a thickness of 10 µm.

Such quartz glass films allow operating temperatures of up to 1000° C., i.e. a high temperature gradient is also possible for cooling purposes. Another advantage of such glass films made from quartz glass is that quartz glass films in this thickness are flexible.

Another possibility would be to produce the apparatus 1 or the inner housing 20 from quartz glass and to produce the exit window 8 from diamond. Here, too, films having a thickness of 10 µm are already known. Such films have a density in the region of 3.5 g/cm$^3$ or 35 g/cm$^2$. The advantage of such films made from diamond is a further improved thermal conductivity, which for example exceeds the thermal conductivity of copper by a factor of 5.

Furthermore, it would also be possible to produce the apparatus 1, i.e. in particular the inner tube or inner housing 20, from metal (e.g. titanium) and to produce the exit window 8, as mentioned above, from diamond having the aforementioned properties. In this case, it would be possible for the exit window 8 to be applied by soldering or fusion. If glass tubes are used, these should advantageously be metallised since discharges can occur over the relatively long distance.

Figure 2:
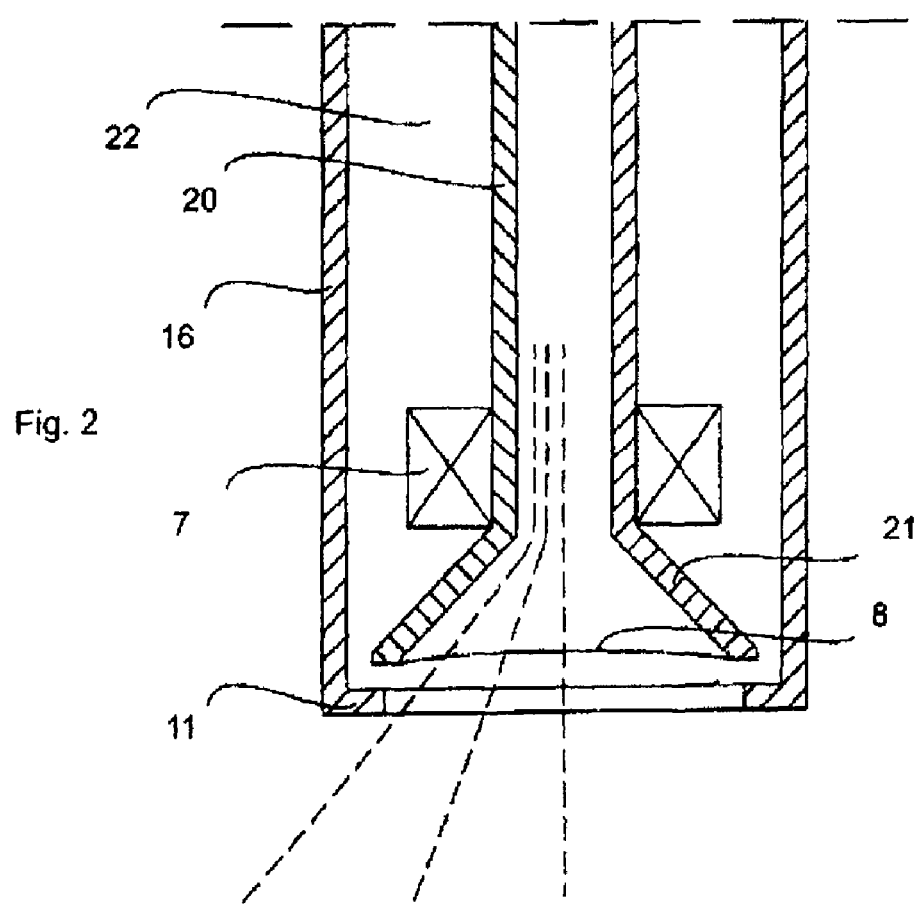
FIG. 2 shows a further embodiment of an apparatus according to the invention.

FIG. 2 shows a further embodiment of an apparatus 1 according to the invention. In this case, the inner housing 20 or inner tube has in the upper region a relatively small inner cross section, which widens in the region of the treatment head 5. In this way, a relatively large chamber 22 is formed between the inner housing 20 and the outer housing 16. In the region of the treatment head 5, the inner housing has an end section 21 widened in a cone shape. By virtue of this end section 21, it is possible to deflect the electron beams by a relatively large angle. In order to deflect the electron beam, use may be made for example of deflection coils 7. Since a further perpendicular coil pair is provided in addition to the coil pair shown in FIG. 2, the electron beams can in principle be emitted in all spatial directions. In the embodiment shown in FIG. 2, only an exit window 8 in the form of a titanium film is provided. However, it would also be possible here to provide a supporting body 26 as shown in FIGS. 1*a* and 1*e*.

Instead of the conical widening shown in FIG. 2, however, the lower region 21 could also be formed for example in a semispherical shape. However, it would also be possible for the deflection coils to be arranged outside the outer housing 16. In addition, it would also be possible to arrange the deflection coils just below the apparatus 1. In the embodiment shown in FIG. 2, the inner housing 20 is also formed of titanium.

Figure 3:
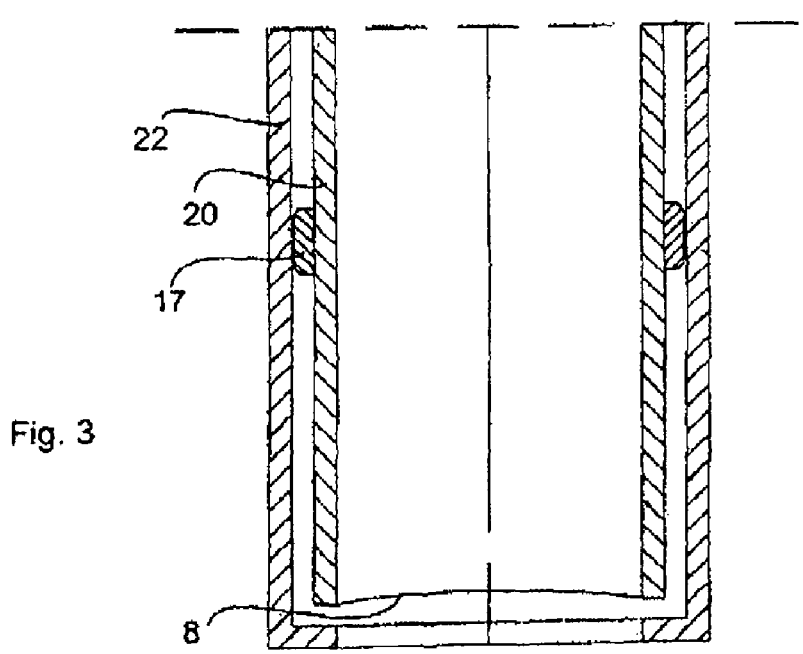
FIG. 3 shows a further embodiment of an apparatus according to the invention.

FIG. 3 shows a further embodiment of an apparatus according to the invention. In this apparatus, a relatively thin air gap 22 is provided between the inner housing 20 and the outer housing 16. In order to prevent contact between the inner housing 20 and the outer housing 16, it is possible to arrange spacers 17 between the two housings 16, 20, wherein the spacers 17 are advantageously electrically insulated. As in the embodiment shown in FIG. 2, deflection coils 7 for deflecting the electron beam could also be provided in the embodiment shown in FIG. 3.

Figure 4:
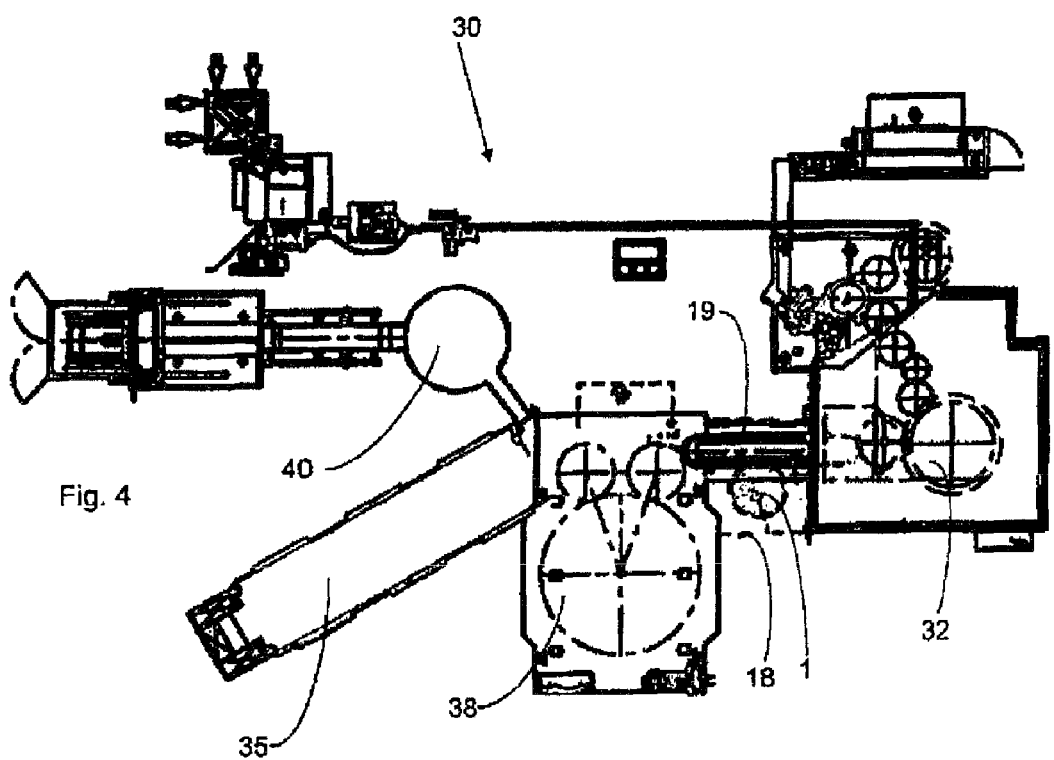
FIG. 4 shows an arrangement for treating containers.

FIG. 4 shows an arrangement according to the invention for treating containers. This arrangement comprises a sorting device 40 for preforms, preferably a sorting device 40 designed as a rotating disc, and also a heating path or an oven 35 in which preforms are heated. This heating path is adjoined by a blowing device 38 which blows the preforms to form containers. Located after this blowing device is a plurality of apparatuses 1 according to the invention for sterilising the containers that have already been blown. Here, reference 18 denotes a shielding device, such as a lead screen, which surrounds the entire apparatus 1 in order to prevent any escape of X-rays.

Reference 19 denotes a transport element which transports the containers from the blowing device 38 to a filling device 32. As seen in the movement direction of the containers, therefore, there is firstly a blowing device 38, then a filling device 32 and possibly then a labelling machine. However, it would also be possible for the blowing device 38 to be followed first by a labelling machine and then by a filling device 32. In the arrangement according to the invention, the apparatus 1 is arranged in each case directly after the blowing device 38.

It would also be possible to provide, in addition to the apparatus 1 according to the invention, also other sterilising apparatuses of a similar type which serve for external cleaning, i.e. for sterilising the outer walls of the containers. For internal sterilisation, the individual containers can be guided onto a rotating unit and then the apparatuses according to the invention can be dipped into the containers. In this case it is advantageous, as mentioned above, to keep the individual apparatuses or emitting fingers at a constant height level and to move the containers relative thereto.

In other words, the emitting fingers 1 for internal sterilisation are dipped into the containers. With particular preference, the individual containers are guided past the individual apparatuses according to the invention while rotating. However, it is also possible to guide the individual containers past a curtain of electron beams, in order thus to achieve external sterilisation.

Figure 5:
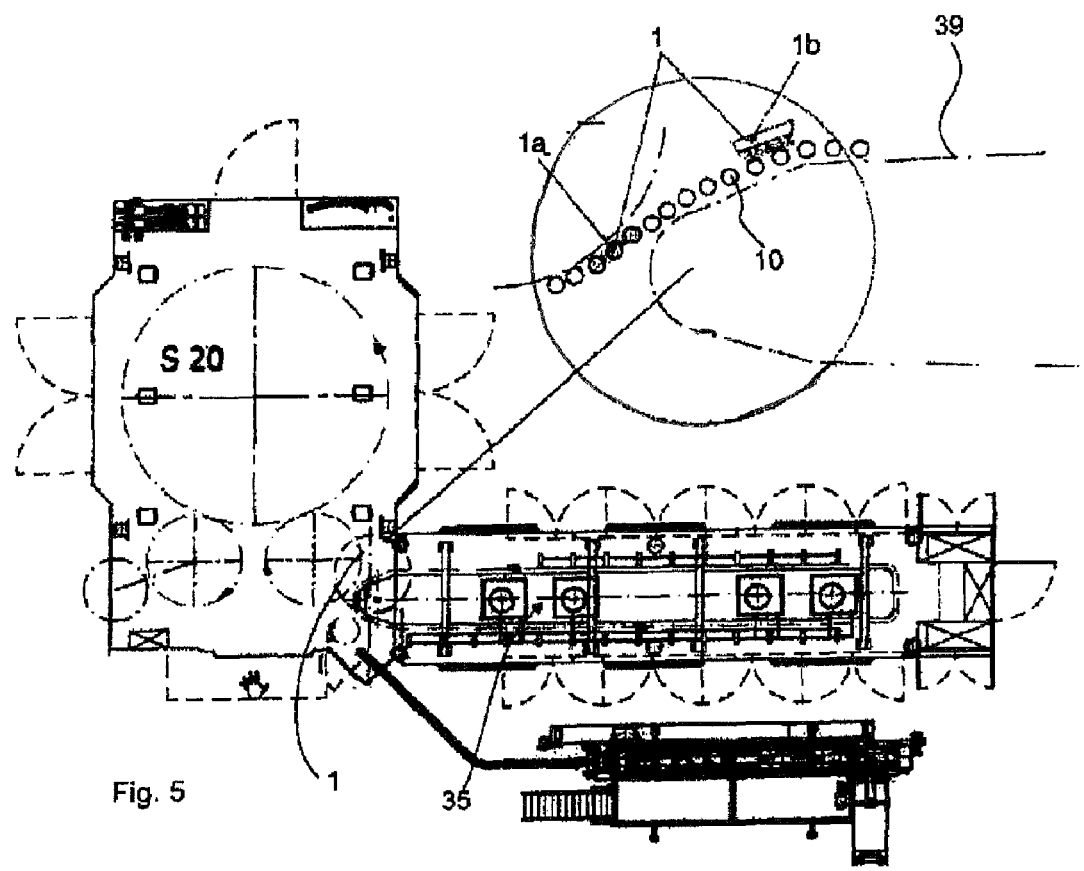
FIG. 5 shows a further example of an arrangement for treating containers.

FIG. 5 shows a detail view of a further arrangement according to the invention for a sterilising apparatus.

In principle, it is possible for the containers to be transported via a chain or to be guided by a chain into a treatment chamber and for emitting fingers to dip into the bottles therein via a lifting movement. However, it would also be possible to transfer the containers to a sterilising device via a star wheel which handles said containers by the neck, and to move the containers over the emitting fingers in said sterilising device by way of a lifting movement.

In the embodiment shown in FIG. 5, firstly an external irradiation of the containers takes place by means of an irradiation device 1b, preferably while the containers rotate. In this case, electron beams accelerated to approx. 150 keV are used for the irradiation. An internal irradiation of the containers is then carried out by the apparatus 1a in the manner described above.

Figure 6:
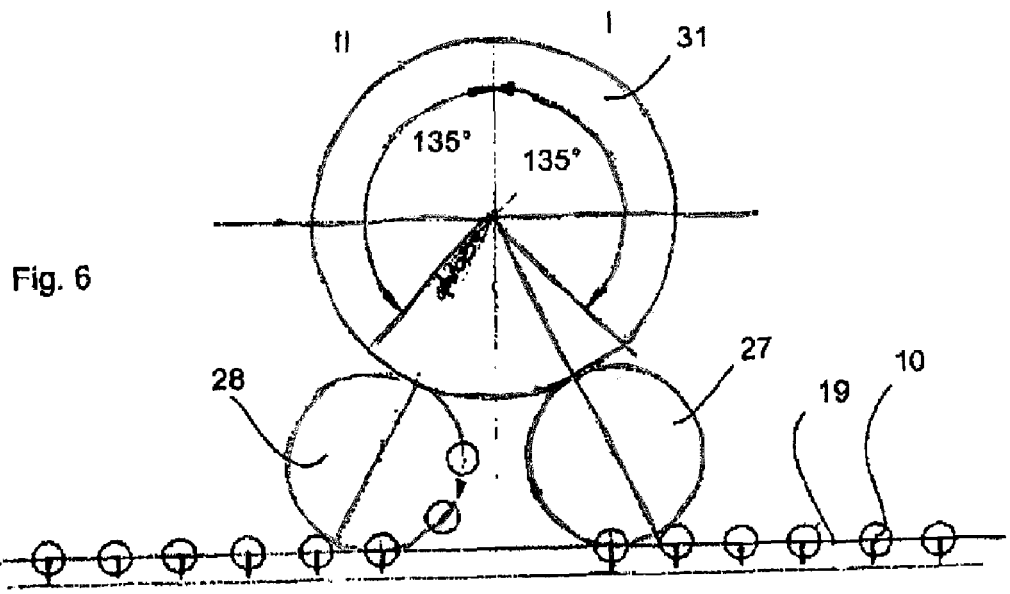
FIG. 6 shows a detail view of an arrangement for treating containers.

FIG. 6 shows a schematic illustration of a method according to the invention for the internal sterilisation of containers 10. The containers 10 are transported via a conveyor belt 19 in the direction of the arrow P and are brought to a sterilising arrangement via an inlet star wheel 27. In a first sector I, firstly the emitting fingers are lowered with a run-out angle of 135° into the interior of the containers 10 or the containers 10 are raised. In a further sector II, the emitting fingers are retracted again or the containers 10 are lowered again. While the emitting fingers are being withdrawn from the containers 10, the apparatus 1 is activated and in this way an internal sterilisation of the containers 10 is carried out.

The containers are then transported away via an outlet star wheel 28.

Figure 7:
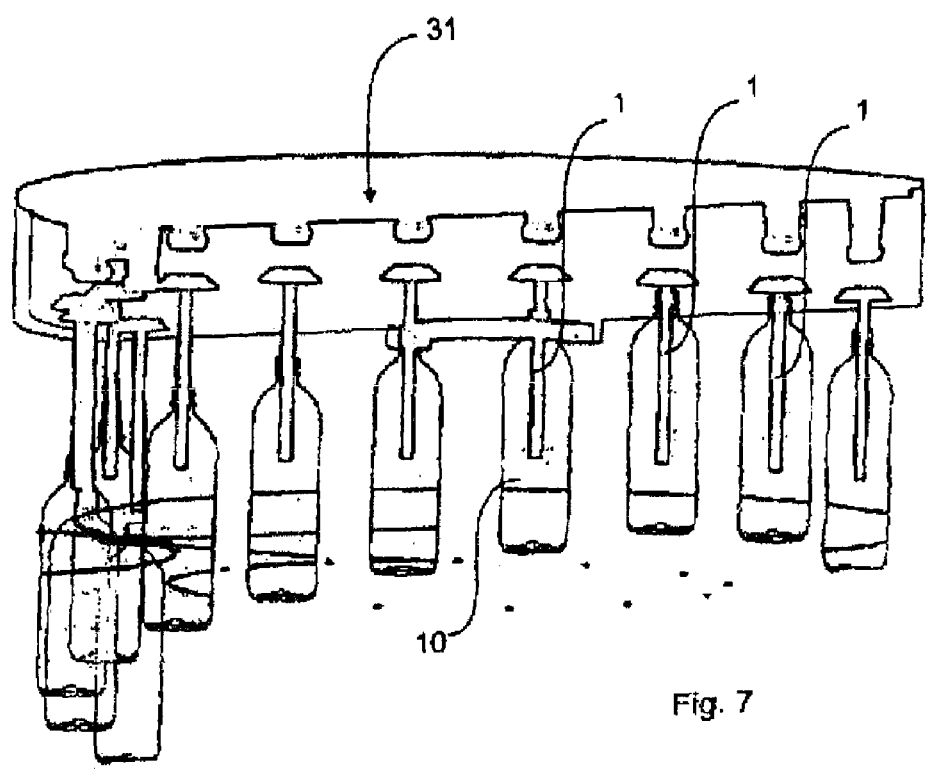
FIG. 7 shows part of a schematic side view of an arrangement for treating containers.

FIG. 7 shows a schematic view of the rotating wheel 31. This rotating wheel 31 comprises a plurality of apparatuses 1 according to the invention which are in each case arranged at the same height, but it can be seen that the individual containers 10 are in each case raised to a maximum position and in this way the apparatuses 1 or the emitting fingers are dipped into the containers 10 to varying depths depending on the rotational position. During this entire process, the apparatuses 1 according to the invention are activated and in this way the inner wall of the containers 10 is sterilised over the entire height of the containers 1. Here, the length of the emitting fingers is selected such that effective sterilisation even of the bottoms of the containers 10 is possible.

Figure 8:
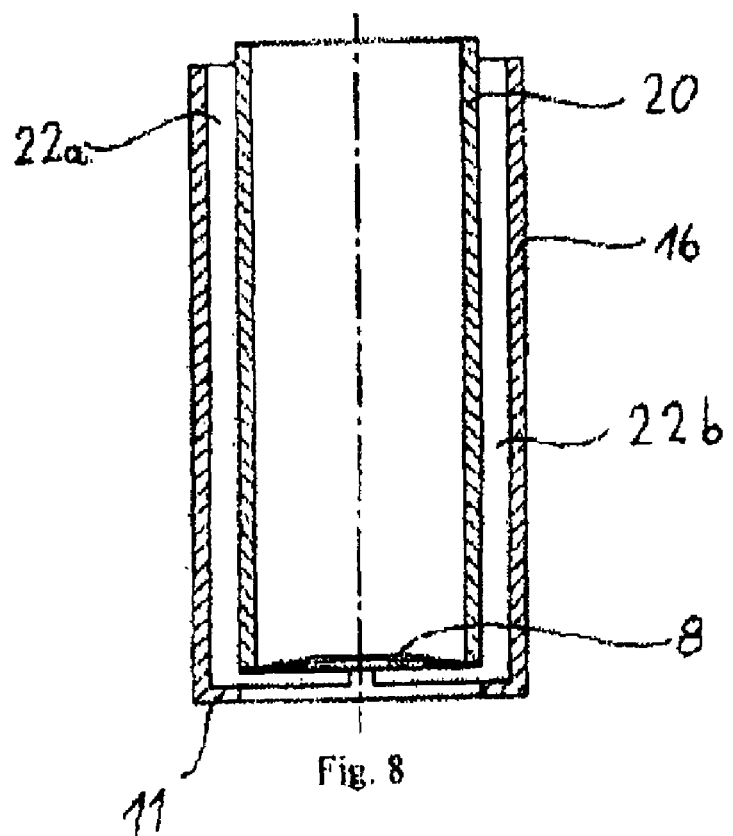
FIG. 8 shows a further embodiment of an apparatus according to the invention.

FIG. 8 shows a further embodiment of an apparatus according to the invention. In this apparatus, the area between the inner housing 20 and the outer housing 16 is designed in such a way that two gas channels 22a and 22b are formed. The gas stream is supplied through one of the two channels 22a and passes laterally across the exit window 8 in a uniform manner. The gas stream can be conveyed away again through the other channel 22b.

Figure 9:
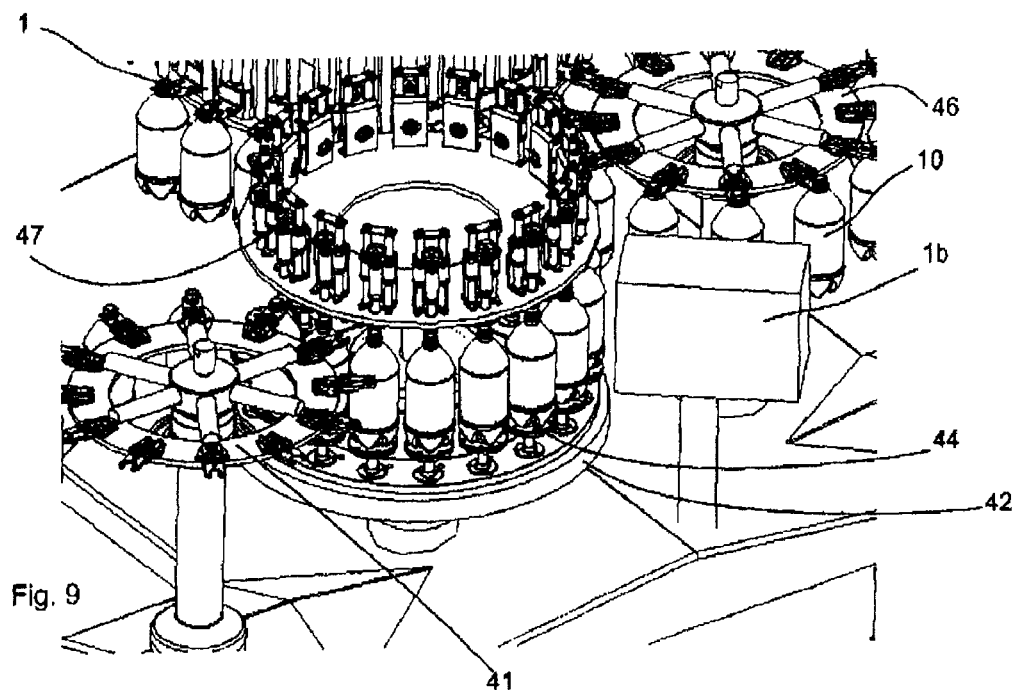
FIG. 9 shows a perspective view of an arrangement according to the invention.

FIG. 9 shows a perspective view of an arrangement according to the invention. Provided upstream of a plurality of apparatuses 1 according to the invention is a further transport carousel 42 on which the containers are transported. Here, the containers are guided past a further sterilising apparatus 1b for containers, and their outer wall is sterilised by this further sterilising apparatus 1b. Then, as mentioned above, the interior of the containers 10 is sterilised.

Reference 44 denotes rotary devices such as rotating plates, by means of which the containers 10 are rotated about their longitudinal direction (or longitudinal axis). By virtue of this rotation, a larger area of the outer periphery of the containers 10 can be sterilised. It would also be possible to provide a plurality of sterilising apparatuses 1b one behind the other in the transport direction of the containers 10.

Figure 10:
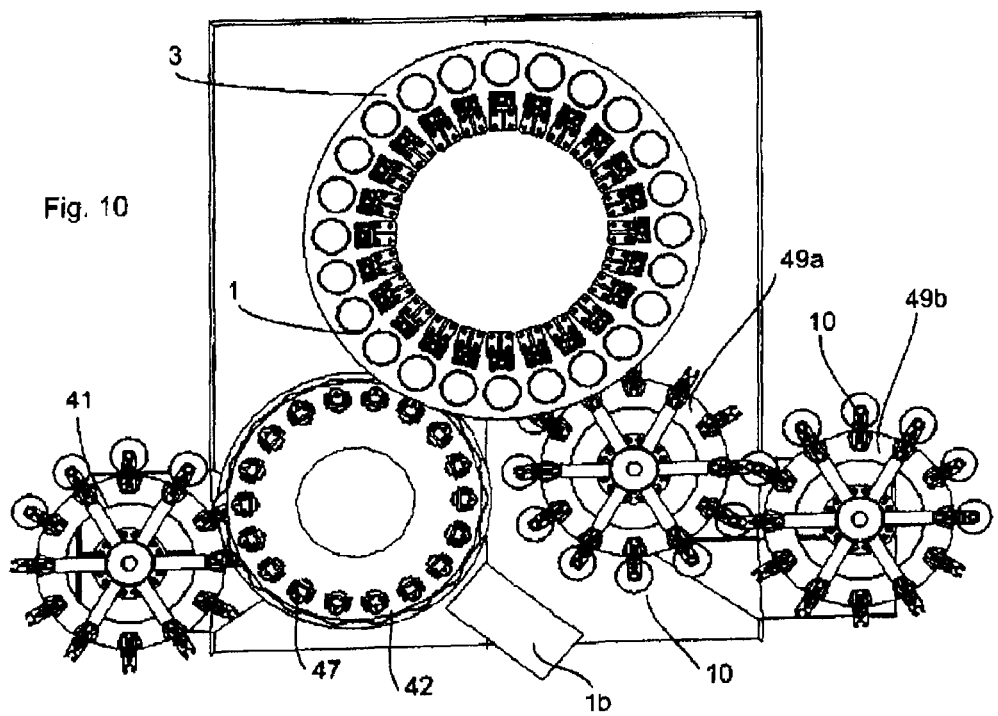
FIG. 10 shows a plan view of the arrangement of FIG. 9.

FIG. 10 shows a plan view of the arrangement of FIG. 9. Provided downstream of a transport wheel 3, on which a plurality of apparatuses 1 for internal sterilisation are provided, are two further transport wheels 49a, 49b which transport the containers out of the arrangement.

Figure 11:
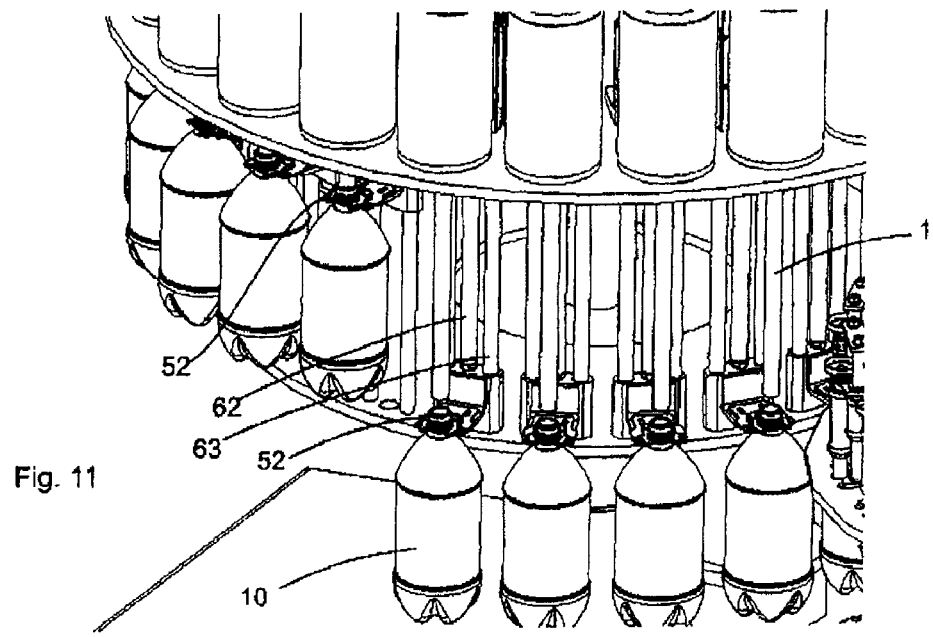
FIG. 11 shows a detail view of the apparatus of FIG. 9.

FIG. 11 shows a detailed view of an apparatus according to the invention. It is possible to see here a plurality of carriers 52, on which the containers 10 are arranged in each case. These carriers 52 are in turn arranged on guide rods 62, and in this way the containers 10 can be moved in their longitudinal direction. The apparatuses 1, which are arranged in a stationary manner, penetrate further into the containers when the containers 10 are lifted. References 63 denote guide rods which guide a movement of the carriers 52. These guide rods 63 are advantageously arranged in a stationary manner.

Figure 12:
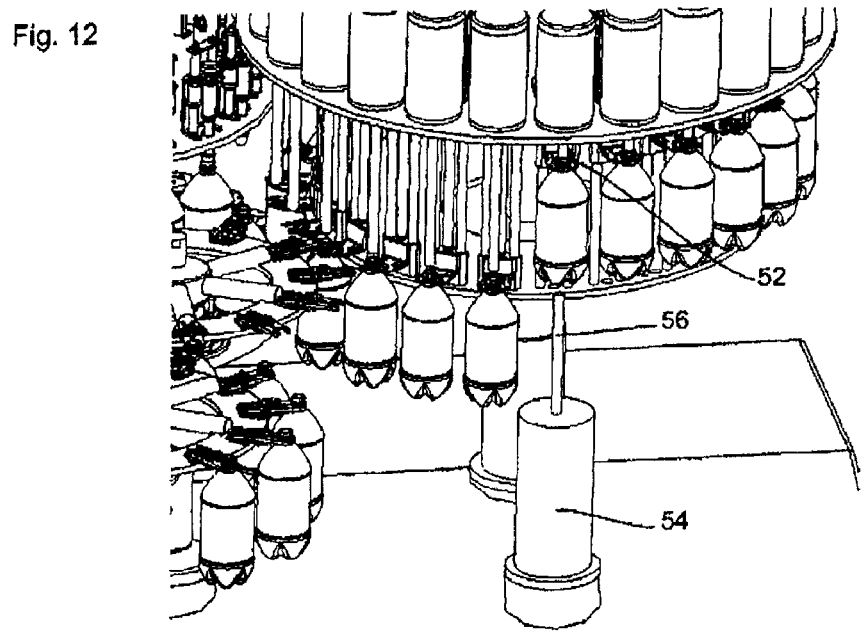
FIG. 12 shows a further detail view of the apparatus of FIG. 9.

FIG. 12 shows a further detail of an arrangement according to the invention. It is possible to see here a further sterilising apparatus 54 which is arranged below the containers and sterilises the base of the containers 10. In this case, this sterilising device 54 also has a rod-like element 56, from the end of which the charge carrier beam can exit. After the containers have been irradiated by this sterilising apparatus 54, the containers 10 are lowered again in their longitudinal direction.

Figure 13:
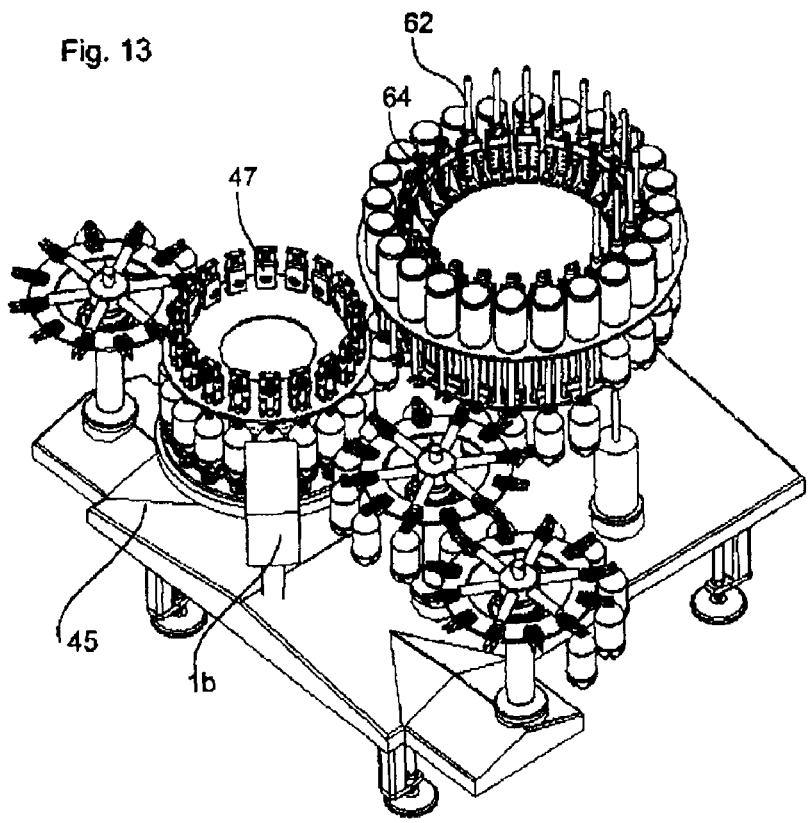
FIG. 13 shows a perspective view of the apparatus of FIG. 9.

FIG. 13 shows a perspective view of an arrangement according to the invention. It can be seen here that the above-described base sterilisation is carried out after the sterilisation of the interior. Reference 45 denotes a support on which the entire arrangement is arranged.

Figure 14:
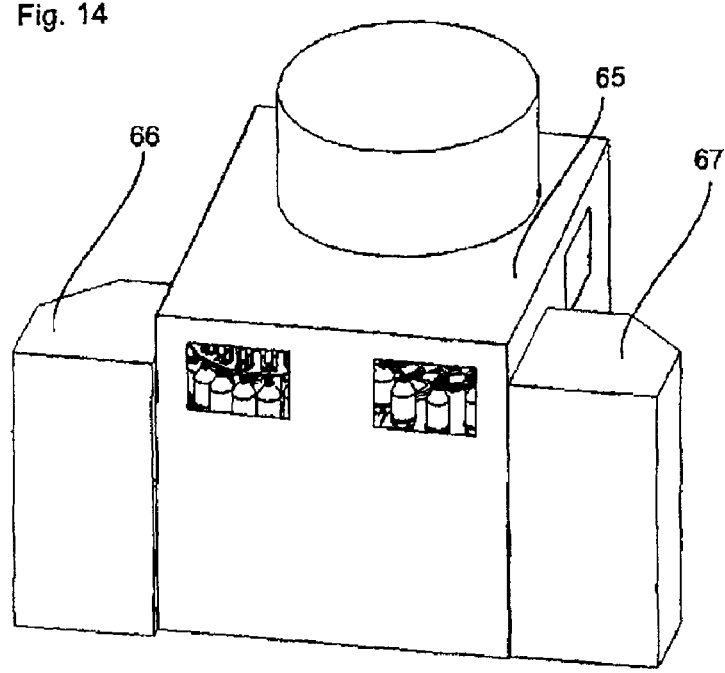
FIG. 14 shows the apparatus of FIG. 13 with a housing.

FIG. 14 shows a further diagram of the arrangement according to the invention. It can be seen that here the individual transport and sterilising apparatuses are arranged in a housing or three housing parts 65, 66, 67. In this way, it is possible to keep the entire apparatus inside a sterile chamber. Interfering radiation can also be screened by the housing parts 65-67.

Figure 15:
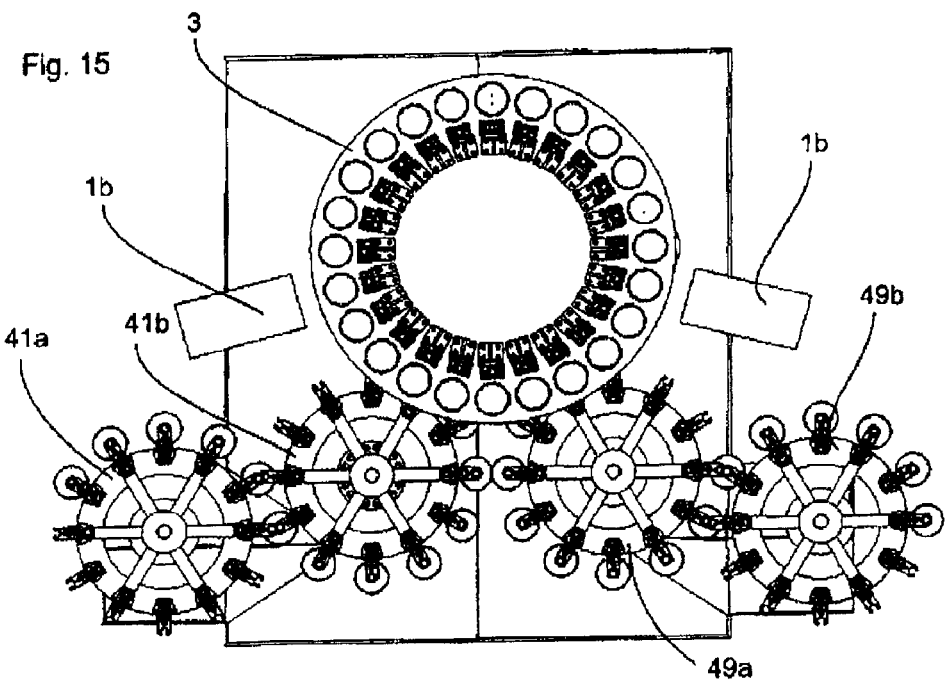
FIG. 15 shows a plan view of an arrangement according to the invention in a further embodiment.

FIG. 15 shows a further embodiment of an arrangement according to the invention. It can be seen here that two sterilising apparatuses 1b are provided which perform the external sterilisation of the containers. Unlike in the embodiments shown above, here the two sterilising apparatuses 1b are not arranged upstream of the transport device 3, on which the internal sterilisation of the containers takes place, but rather around said transport device 3.

More specifically, in the embodiment shown in FIG. 15, the sterilisation of the outer wall takes place both (immediately) before the sterilisation of the inner wall and (immediately) thereafter. References 41a and 41b denote transport star wheels which supply the containers 10 to the transport device 3 and references 49a and 49b denote transport star wheels which transport the containers 10 away again.

Figure 16:
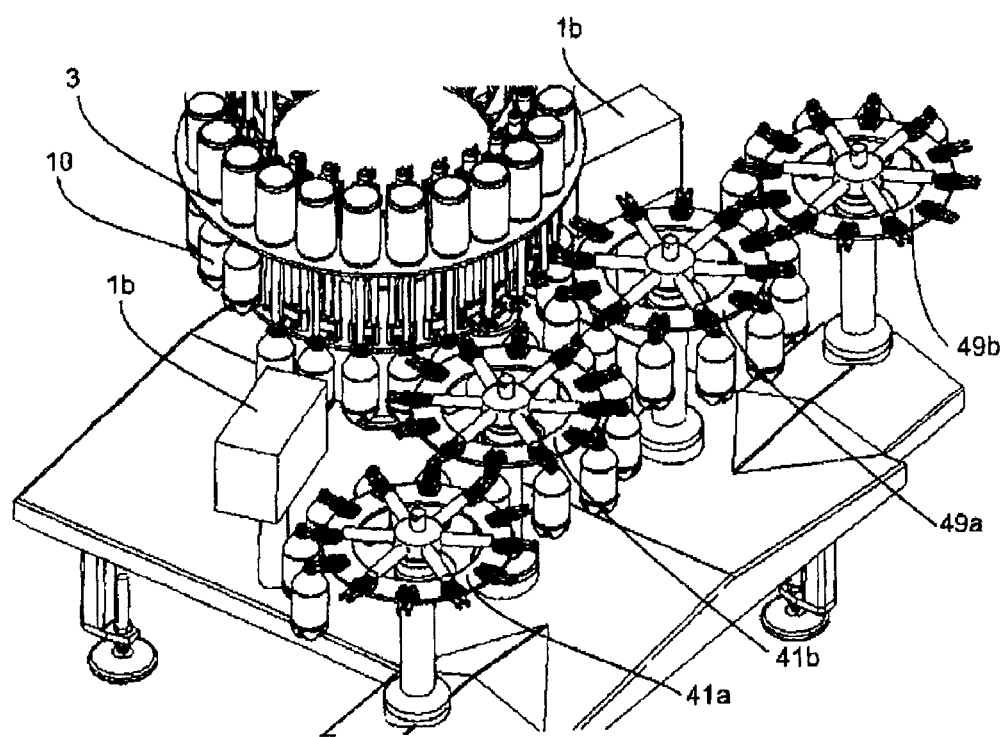
FIG. 16 shows a perspective view of the apparatus of FIG. 15.

FIG. 16 shows a perspective view of the apparatus shown in FIG. 15. It can be seen that firstly a sterilisation of the outer surface of the containers is carried out by the sterilising apparatus 1b shown on the left, with the containers preferably being rotated through approx. 180° in this region. The containers are then raised in order to carry out sterilisation of the interior. Thereafter, the containers are lowered again and the outer circumference is sterilised once more by the sterilising apparatus shown on the right, with the containers preferably being rotated through a further 180°. It would also be possible to rotate the containers 10 also during the internal sterilisation.

Preferably, therefore, corresponding rotating devices are adapted to one another in such a way that the two sterilising apparatuses 1b can perform a complete external sterilisation of the containers 10. As a result, just one carousel is used here for the external/internal sterilisation. By providing two sterilising apparatuses 1b, the rotational speed of the containers 10 which is required for the external sterilisation can be reduced. The arrangement shown in FIGS. 15 and 16 thus allows a greater space saving.

All the features disclosed in the application documents are claimed as essential to the invention in so far as they are novel individually or in combination with respect to the prior art.

The invention claimed is:

1. An apparatus for sterilizing containers, comprising:
   an inner housing containing a treatment head, the inner housing having at its distal end an exit window with a face through which a charge carrier can pass; and
   an outer housing substantially surrounding the inner housing and at least partially defining a chamber circumferentially around the tubular inner housing in form of one or a plurality of channels in which a gaseous medium may be guided past the face of the exit window and which extends as far as the treatment head, wherein the outer housing is dimensioned such that the outer housing can be guided through the mouth of the container into the container to allow the treatment head to be guided into the container to aim the charge carrier onto an inner wall of the container, wherein the outer housing has an opening proximal to the exit window such that the gaseous medium is guided along the tubular inner housing to exit the chamber, wherein the outer housing is formed in such a way that the gaseous medium is guided also in a radial direction of the apparatus past the exit window and wherein the apparatus is surrounded by a shielding device in order to prevent escape of any X-ray radiation.

2. The apparatus according to claim 1, wherein the treatment head comprises a source of the charge carrier, and an accelerator to accelerate the charge carrier in a direction toward the exit window.

3. The apparatus according to claim 1, wherein the apparatus comprises a support coupled to the exit window, wherein the support is cooled by the fluid medium.

4. The apparatus according to claim 1, wherein the chamber comprises one or more channels, through which the fluid medium can be passed.

5. The apparatus according to claim 4, wherein the fluid medium is selected from a group of gaseous media comprising helium, nitrogen, argon, carbon dioxide, and a mixture thereof.

6. The apparatus according to claim 4, wherein the fluid medium is selected from a group of liquid media comprising water, oil, and liquid nitrogen.

7. The apparatus according to claim 1, wherein the fluid medium is selected from a group of gaseous media comprising helium, nitrogen, argon, carbon dioxide, and a mixture thereof.

8. The apparatus according to claim 1, wherein the exit window is made from a material selected from a group of materials comprising titanium, quartz glass, diamond, and a combination thereof.

9. The apparatus according to claim 1, wherein the exit window has a thickness which is between a range selected from the group of between 3 µm and 30 µm, between 4 µm and 25 µm, and between 5 µm and 20 µm.

10. The apparatus according to claim 1, wherein the apparatus comprises a deflection device for deflecting the charge carrier.

11. The apparatus according to claim 1, wherein the treatment head is moveable relative to the container in a longitudinal direction of the container.

12. The apparatus according to claim 1, wherein the treatment head is rotatable relative to the container.

13. The apparatus according to claim 1, wherein the treatment head is moveable in a radial direction of the container.

14. A system for treating containers which includes a sterilizing apparatus as claimed in claim 1.

15. The system according to claim 14, wherein the system comprises a filler to fill the containers and the apparatus is arranged upstream of the filler.

16. The system according to claim 14, wherein the system comprises a displacer that displaces the containers in the longitudinal direction of the containers relative to the apparatus.

17. The system according to claim 14, wherein the apparatus is arranged between an expander for the containers and the filler.

18. The system according to claim 14, wherein the system comprises a plurality of apparatuses for sterilizing containers, wherein the plurality of apparatuses are arranged along a circular path.

19. The system according to claim 14, wherein the system further comprises an outer sterilizer to sterilize an outer wall of the containers.

20. The system according to claim 19, wherein the outer sterilizer is arranged upstream of the sterilizing apparatus.

21. The system according to claim 19, wherein the outer sterilizer is arranged in a stationary manner.

22. The system according to claim 19, wherein the system comprises a transport carousel for conveying the containers past the outer sterilizer.

23. The system according to claim 22, wherein the transport carousel comprises rotary devices for rotating the containers about their longitudinal axis.

24. The apparatus according to claim 1 wherein the apparatus comprises an accelerator to accelerate the charge carrier in a direction toward the exit window of the inner housing.

25. The apparatus according to claim 1, wherein the treatment head is provided at the lower end of the housing.

26. The apparatus according to claim 1 wherein the electrons are accelerated to energy in a range from 100 keV-200 keV.

27. The apparatus according to claim 1, wherein the apparatus has a cross section with a diameter of less than 30 mm.

28. The apparatus according to claim 1, wherein the shielding device is a lead screen.

29. The apparatus according to claim 1, wherein the chamber also extends in a longitudinal direction of the inner housing.

30. A method for sterilizing containers, comprising generating a charge carrier and accelerating the charge carrier in the direction of an exit window which is arranged in an inner housing of a treatment head which further comprises an outer housing substantially surrounding the inner tubular housing and at least partially defining a chamber circumferentially around the inner tubular housing and in which a gaseous medium may be guided past the face of the exit window, introducing the treatment head and its outer housing which is dimensioned such that it can be guided through the mouth of the container through a mouth of the container into the interior of the container, aiming accelerated charge carriers from the treatment head onto the inner wall of the container, moving the container relative to the treatment head, and guiding the gaseous medium in the chamber in a radial direction of the treatment head past the exit window of the treatment head, wherein the outer housing has an opening proximal to the exit window such that the gaseous medium is guided to exit the chamber, and wherein the apparatus is surrounded by a shielding device in order to prevent escape of any X-ray radiation.

31. The method according to claim 30, wherein the charge carriers are deflected in a radial direction of the container before reaching the exit window.

32. The method according to claim 30, wherein the charge carriers are deflected in a radial direction of the container after exiting through the exit window.

33. The method according to claim 30, wherein the exit window is cooled.

34. The method according to claim 33, wherein the fluid medium cools the exit window.

* * * * *